US011058545B2

(12) United States Patent
Carioscia

(10) Patent No.: US 11,058,545 B2
(45) Date of Patent: Jul. 13, 2021

(54) FIRST METATARSOPHALANGEAL JOINT IMPLANT AND METHOD FOR PLACEMENT

(71) Applicant: George J. Carioscia, Bloomingdale, IL (US)

(72) Inventor: George J. Carioscia, Bloomingdale, IL (US)

(73) Assignee: Dura-Trac Implants LLC, Bloomingdale, IL (US)

( * ) Notice: Subject to any disclaimer, the term of this patent is extended or adjusted under 35 U.S.C. 154(b) by 43 days.

(21) Appl. No.: 16/230,999

(22) Filed: Dec. 21, 2018

(65) Prior Publication Data

US 2019/0358048 A1 Nov. 28, 2019

Related U.S. Application Data

(60) Provisional application No. 62/677,110, filed on May 28, 2018, provisional application No. 62/718,852, filed on Aug. 14, 2018.

(51) Int. Cl.
*A61F 2/42* (2006.01)

(52) U.S. Cl.
CPC .... *A61F 2/4225* (2013.01); *A61F 2002/4233* (2013.01)

(58) Field of Classification Search
CPC ................................ A61F 2/42; A61F 2/4225
See application file for complete search history.

(56) References Cited

U.S. PATENT DOCUMENTS

2010/0249942 A1* 9/2010 Goswami .............. A61F 2/4225 623/21.19
2011/0257755 A1* 10/2011 Bellemere ............. A61F 2/4241 623/21.15

OTHER PUBLICATIONS

John Vanore, "Implants", webpage on "Musculoskeletal Key" online insight engineer, available at: https://musculoskeletalkey.com/implants/ (11 pages). Webpage indicates that it was posted by Musculoskeletal Medicine, on Jul. 26, 2016.

* cited by examiner

*Primary Examiner* — Matthew W Schall
(74) *Attorney, Agent, or Firm* — Kaspar Law Company, LLC; Scott R. Kaspar

(57) ABSTRACT

An implant is disclosed for the first metatarsophalangeal joint between the proximal phalange and the first metatarsal, the phalange moving in a sagittal plane perpendicular to a transverse plane. The implant includes a metatarsal component for securing against the distal end of the first metatarsal, the metatarsal component having an interfacing surface with a plurality of ridges and valleys. The implant further includes a phalangeal component for securing against the proximal end of the proximal phalange, the phalangeal component having an interfacing surface with a plurality of ridges and valleys, wherein the ridges of the interfacing surface of the metatarsal component are received by the valleys of the interfacing surface of the phalangeal component to provide for a full range of motion in the sagittal plane but impede motion in the transverse plane.

15 Claims, 14 Drawing Sheets

FIRST METATARSOPHALANGEAL JOINT IMPLANT AND METHOD FOR PLACEMENT

RELATED APPLICATIONS

This application claims the benefit of priority of U.S. Provisional Patent Application No. 62/677,110, filed May 28, 2018, and U.S. Provisional Patent Application No. 62/718,852, filed Aug. 14, 2018, both of which are hereby incorporated by reference herein in their entireties.

TECHNICAL FIELD

The present invention relates to a joint implant, and more particularly, an implant for the first metatarsophalangeal joint, and a method for its placement.

BACKGROUND

The metatarsophalangeal joint, which is the bone joint between the first metatarsal and proximal phalange of the hallux or great toe, in some patients has been found to deteriorate due to deformity of the bones or disease or disorder of the joint, such as rheumatoid arthritis, both of which can cause pain and inflammation of the joint, as well as reduction of a patient's range of motion. Over about the past four decades, joint implants have been introduced to correct deformity, reduce pain, and restore a patient's range of motion.

Presently, many of the implants placed in the metatarsophalangeal joint are two-system implants often referred to as a "ball-and-cup" design. Such implants typically comprise a metatarsal component having a rounded or ball-shaped head that engages with a cupped portion of a phalangeal component. In this arrangement, a full range of motion can be restored, as the cupped portion can rotate about the ball-shaped head in most any direction, including in a transverse plane. An example of a conventional joint implant of this type is the "ReFlexion" implant system manufactured and sold by OsteoMed. Joint implants of this type are installed with compression-fit stems that engage with the bone and do not use any screws.

In 1967, Swanson introduced a silicone implant, sometimes referred to as "hemi-implant," having a base or collar portion attached to a stem that inserts into the proximal phalange. The base of the silicone implant serves as the base of the proximal phalange and is concave to fit the head of the first metatarsal. Swanson later introduced in 1977 a double-stemmed hinged silicone implant that effectively connects the proximal phalange and the first metatarsal. The silicone used in many of the Swanson-type implants was a high-performance medical grade material developed and manufactured by Dow Corning Company that was thought to be biocompatible. The primary criticism of the Swanson-type implants is that silicone degrades over time and in some cases is not biocompatible, requiring replacement and/or other restoration of the metatarsophalangeal joint.

While the prior art metatarsophalangeal joint implants may eliminate or reduce pain and inflammation, thereby increasing a patient's range of motion, the prior art implants do not provide for control of motion in the transverse plane. As a result, prior art joint implants do not provide for long-term correction of certain deformities or deviation of the bone structure of the great toe.

SUMMARY OF THE INVENTION

According to one non-limiting aspect of the present disclosure, a first example embodiment of an implant is disclosed for the first metatarsophalangeal joint between the proximal phalange and the first metatarsal, the phalange moving in a sagittal plane perpendicular to a transverse plane. The implant includes a metatarsal component for securing against the distal end of the first metatarsal, the metatarsal component having an interfacing surface with a plurality of ridges and valleys. The implant further includes a phalangeal component for securing against the proximal end of the proximal phalange, the phalangeal component having an interfacing surface with a plurality of ridges and valleys, wherein the ridges of the interfacing surface of the metatarsal component are received by the valleys of the interfacing surface of the phalangeal component to provide for a full range of motion in the sagittal plane but impede motion in the transverse plane.

According to another non-limiting aspect of the present disclosure, a second example embodiment of an implant is disclosed for the first metatarsophalangeal joint between the proximal phalange and the first metatarsal, the proximal phalange proximally located to the distal phalange and both phalanges moving in a sagittal plane perpendicular to a transverse plane. The implant includes a metatarsal component for securing against the distal end of the first metatarsal, the metatarsal component having an interfacing surface with a plurality of ridges and valleys. The implant also includes a cannulated phalangeal component for abutting against the proximal end of the proximal phalange, the phalangeal component having an interfacing surface with a plurality of ridges and valleys and further having a threaded stem for receiving a headed or headless screw to secure the phalangeal component to the proximal and distal phalanges thereby making it one phalangeal member, wherein the ridges of the interfacing surface of the metatarsal component are received by the valleys of the interfacing surface of the phalangeal component to provide for a full range of motion in the sagittal plane but impede motion in the transverse plane.

According to yet another non-limiting aspect of the present disclosure, a third example embodiment of an implant is disclosed for the first metatarsophalangeal joint between the proximal phalange and the first metatarsal, the proximal phalange located proximally to the distal phalange and both phalanges moving in a sagittal plane perpendicular to a transverse plane. The implant includes a metatarsal component for securing against the distal end of the first metatarsal, the metatarsal component having an interfacing surface with a plurality of ridges and valleys, a cannulated phalangeal component for abutting the proximal end of the proximal phalange, the phalangeal component having an interfacing surface with a plurality of ridges and valleys, the phalangeal component further having a stem for insertion into the proximal end of the proximal phalange, a threaded insert for insertion into the proximal end of the distal phalange, and a screw passing through the proximal phalange and received by the threaded insert placed within the distal phalange for securing the proximal and distal phalanges either to correct angulation of the proximal and distal phalanges or to fuse the hallux interphalangeal joint, wherein the ridges of the interfacing surface of the metatarsal component are received by the valleys of the interfacing surface of the phalangeal component to provide for a full range of motion in the sagittal plane but impede motion in the transverse plane.

According to still another non-limiting aspect of the present disclosure, yet another example embodiment of an implant is disclosed for the first metatarsophalangeal joint between the proximal phalange and the first metatarsal, the proximal phalange located proximally to the distal phalange and both phalanges moving in a sagittal plane perpendicular to a transverse plane. The implant includes a metatarsal component for securing against the distal end of the first metatarsal, the metatarsal component having an interfacing surface with a plurality of ridges and valleys, a cannulated phalangeal component for abutting the proximal end of the proximal phalange, the phalangeal component having an interfacing surface with a plurality of ridges and valleys, the phalangeal component further having a stem for insertion into the proximal end of the proximal phalange, and a bone screw passing through the proximal phalange and anchored within the distal phalange for securing the proximal and distal phalanges either to correct angulation of the proximal and distal phalanges or to fuse the hallux interphalangeal joint, wherein the ridges of the interfacing surface of the metatarsal component are received by the valleys of the interfacing surface of the phalangeal component to provide for a full range of motion in the sagittal plane but impede motion in the transverse plane.

According to still yet another non-limiting aspect of the present disclosure, an example embodiment of a method for placement of a first metatarsophalangeal joint implant having metatarsal and phalangeal components is disclosed, wherein a threaded insert is secured within the distal phalange and a guide wire is put through the threaded insert out through the distal phalange and retrograded back into the proximal phalange to measure for the appropriate length of screw required to secure the implant to the proximal and distal phalanges, thereby fusing the interphalangeal joint. Alternatively, a bone screw may be used for anchoring within the distal phalange such that a threaded insert is not necessary. In such an embodiment, the guide wire is put through the base of the distal phalange out through the distal aspect and retrograded back into the proximal phalange and into the implant. A clinician may use a measuring device to measure the retrograded portion of the guide wire to determine the appropriate length of bone screw to use. Then, the clinician may modify the interphalangeal joint by cutting or removing a wedge of bone and/or cartilage (Akin osteotomy) as necessary to change the direction of the hallux to get a straighter pull on the tendons that work the metatarsophalangeal joint so that the hallux is lined up with the metatarsal as the bone screw is tightened to fuse the interphalangeal joint.

Additional features and advantages are described herein, and will be apparent from the following Detailed Description and the figures.

BRIEF DESCRIPTION OF THE DRAWINGS

Features and advantages of the joint implant and method for implantation described herein may be better understood by reference to the accompanying drawings in which.

The reader will appreciate the foregoing details, as well as others, upon considering the following Detailed Description of certain non-limiting embodiments of the joint implant and method of implantation, according to the present disclosure. The reader may also comprehend certain of such additional details upon implantation and use of the joint implant described herein. The reader will appreciate that the Figures depict the claimed joint implant as it is placed in a model of the first metatarsophalangeal joint, which was selected for demonstrative purposes only. Those skilled in the art will understand that the claimed joint implant is intended for placement in a first metatarsophalangeal joint of a human being, for treatment of the medical conditions described herein.

DETAILED DESCRIPTION

The present disclosure, in part, is directed to a first metatarsophalangeal joint implant and methods for its implantation.

Figure 1:
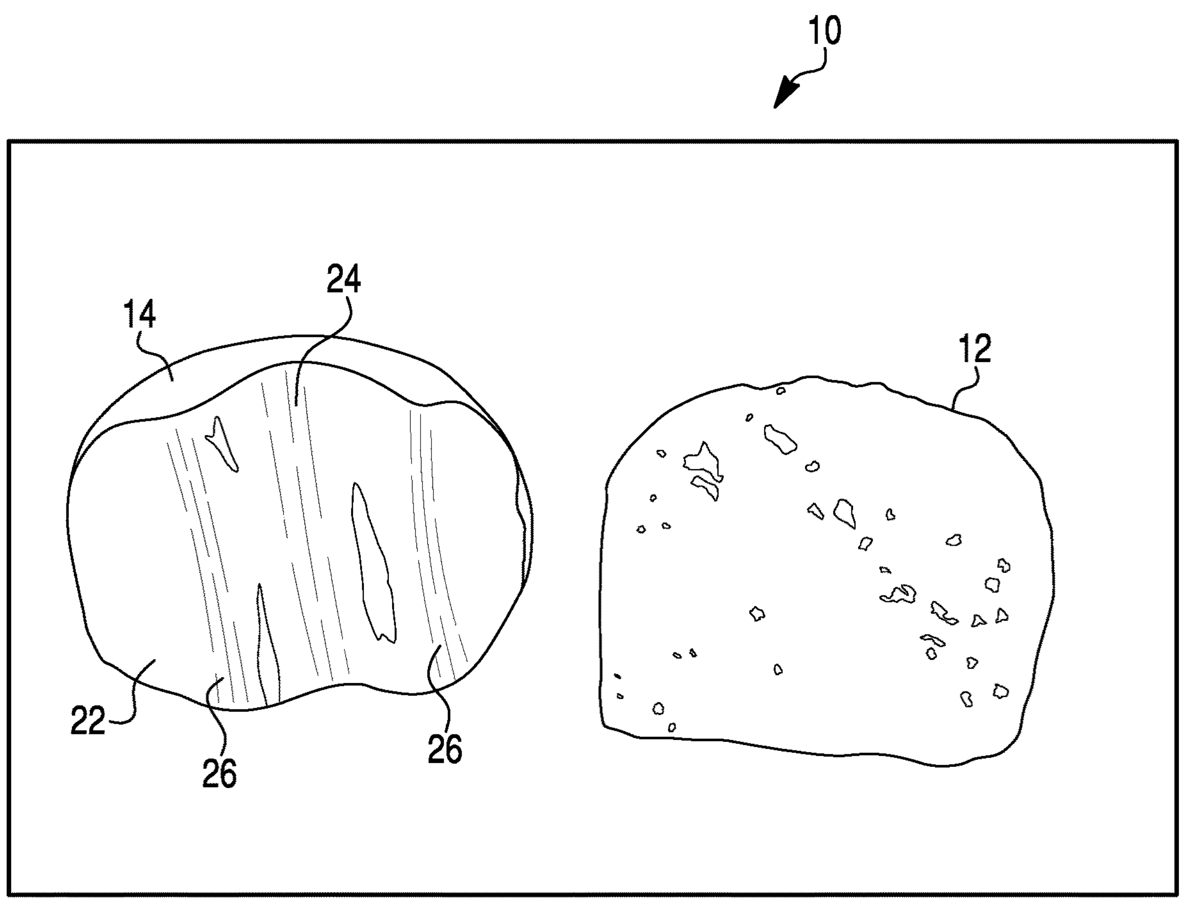
FIG. 1 depicts a first exemplar of an implant for the first metatarsophalangeal joint of the present invention.
Figure 2:
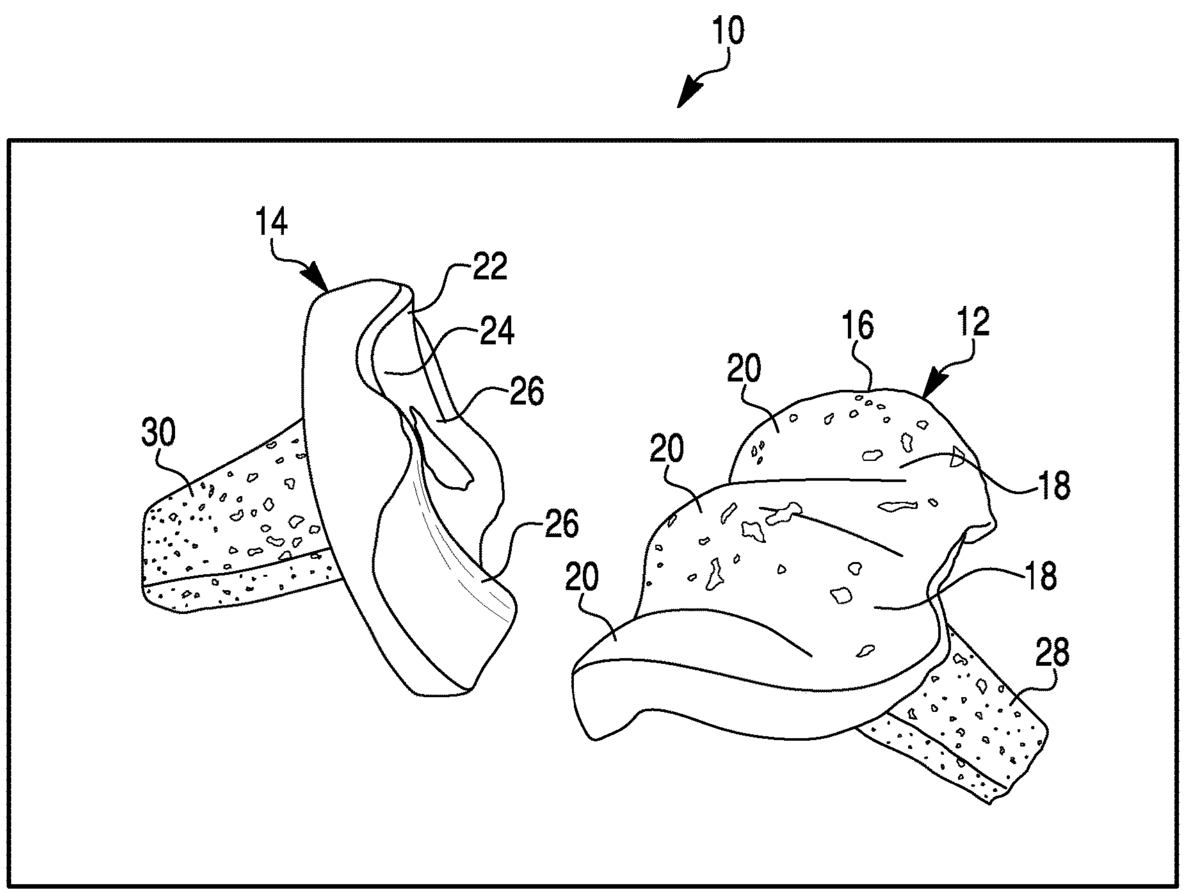
FIG. 2 depicts another view of the exemplar joint implant of FIG. 1.

As shown in FIGS. 1 and 2, a first embodiment of an implant (10) for the first metatarsophalangeal joint is disclosed. The joint implant (10) comprises two components, a metatarsal component (12) and a phalangeal component (14). The metatarsal component (12) has an interfacing surface (16) that is ridged to include two valleys (18) and three ridges (20). The phalangeal component (14) has an interfacing surface (22) with a central valley (24) and two ridges (26) that each form a partial valley on the side. The metatarsal component (12) has a stem (28) for engaging with the metatarsal during placement, and the phalangeal component (14) has a stem (30) for engaging with the proximal phalange during placement. The stems (28, 30) of both components (12, 14) are compression or press-fit within the bone.

During placement, the interfacing surface (16) of the metatarsal component (12) is received by the interfacing surface (22) of the phalangeal component (14) such that the central valley (24) of the phalangeal component (14) cradles the central ridge (20) of the metatarsal component (12), and the two ridges (26) of the phalangeal component (14) are cradled by the two valleys (18) of the metatarsal component (12). The engagement of the two interfacing surfaces (16, 22) allows for the phalangeal component (14) to glide and pivot in a sagittal plane with respect to the metatarsal component (12), but impedes movement in a transverse plane because of the ridge-and-valley structure. As such, when the components (12, 14) are placed, the proximal phalange has a wide range of motion in the sagittal plane, but only a limited range of motion in the transverse plane, a benefit that is described more fully hereafter.

The components (12, 14) may be constructed of any appropriate biomaterial, including stainless steel, cobalt chromium alloy, chemically-pure titanium, titantium alloys, certain polymers, such as polyethylene (UHMW) and polymethylmethacrylate, silicone, certain ceramics, and carbon. In a preferred embodiment, the metatarsal component (12) is made of a cobalt chromium alloy, which is known to have excellent compressive strength, making it suitable for bearing surfaces such as interfacing surface (16), while the phalangeal component (14) is made of a UHMW material. Research tends to show that fabricating the components (12, 14) of different materials tends to enhance the longevity of the implant.

One or more of the stems (28, 30) of the components (12, 14) may be powdered or coated with any appropriate material, including hydroxyapatite, porous titanium, calcium carbonate, and cobalt chromium. Applying such a coating to the stem is known to provide greater osteo-integration between the stem and the bone. One or more of the stems (28, 30) of components (12, 14) also may be serrated, to provide for stronger bone engagement and/or osteo-integration with the bone. The shape of the stems (28, 30) may be rounded, triangular, square, or any other shape as may be appropriate to engage with the bone.

The joint implant (10) depicted in FIGS. 1 and 2 is intended for use in a first metatarsophalangeal joint where the sesamoid bones (32) are still freely moving with respect to the metatarsal (34). That is, the sesamoids (32) have not fibrosed or fused to the metatarsal (34), which may occur with patients suffering from rheumatoid arthritis, among other joint diseases or disorders.

Figure 3:
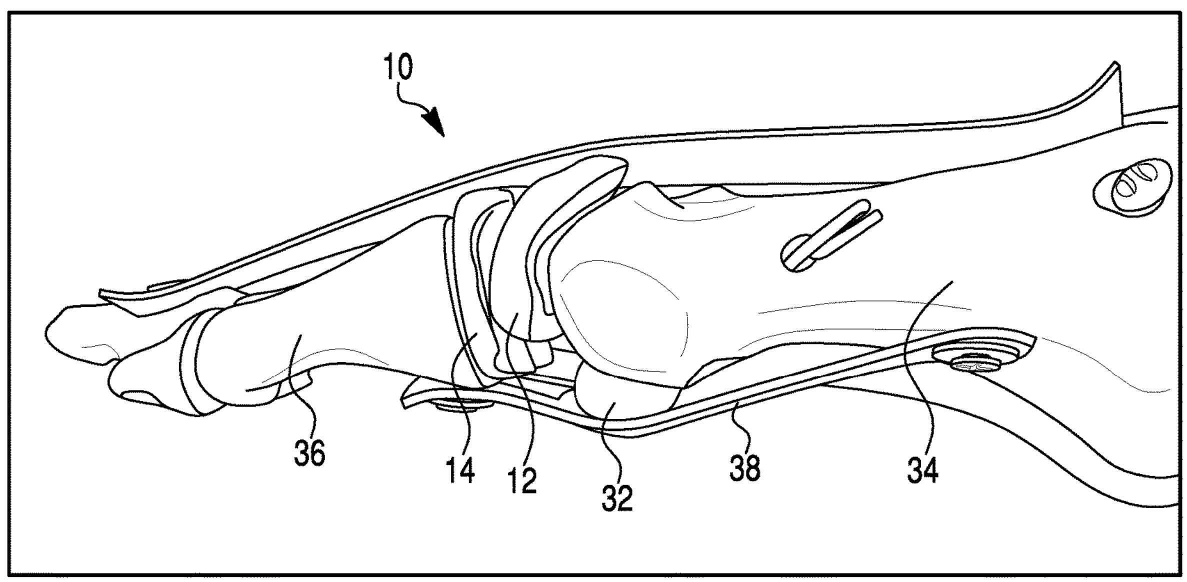
FIG. 3 depicts a side view of a model of the first metatarsal and proximal phalange with the exemplar joint implant of FIG. 1 placed at the first metatarsophalangeal joint of said model.

As shown in FIG. 3, joint implant (10) is disclosed being placed in the first metatarsophalangeal joint, with metatarsal component (12) press-fit into the metatarsal (34) and phalangeal component (14) press-fit into the proximal phalange (36). Joint implant (10) is appropriate where, as shown in FIGS. 3-5, the sesamoid (32) has not fibrosed to the metatarsal (34) and, as such, a clinician would prefer to maintain the tendon structure, particularly the flexor hallucis brevis (38), which attaches to the underside of the base of the proximal phalange (36).

Figure 4:
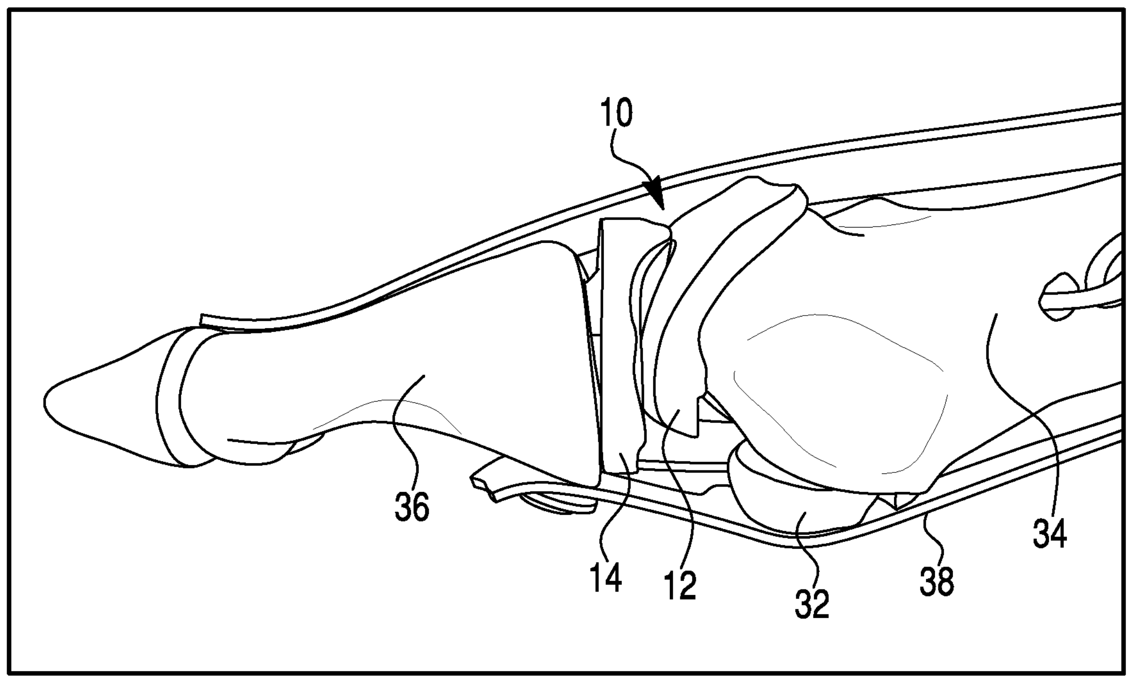
FIG. 4 depicts a side view of the first metatarsal and proximal phalange model with the exemplar joint implant of FIG. 1 placed at the first metatarsophalangeal joint, with the phalanges aligned in the sagittal plane.

As shown in FIG. 4, the joint implant (10) is disclosed as placed when the metatarsal (34) and proximal phalange (36) are in the same sagittal plane. That is, the patient's foot is generally flat or in a resting position and there is no plantar flexion. In this arrangement, the metatarsal component (12) and phalangeal component (14) are fully engaged about the interfacing surfaces (16, 22). The sesamoid bone (32) also is in a resting position.

Figure 5:
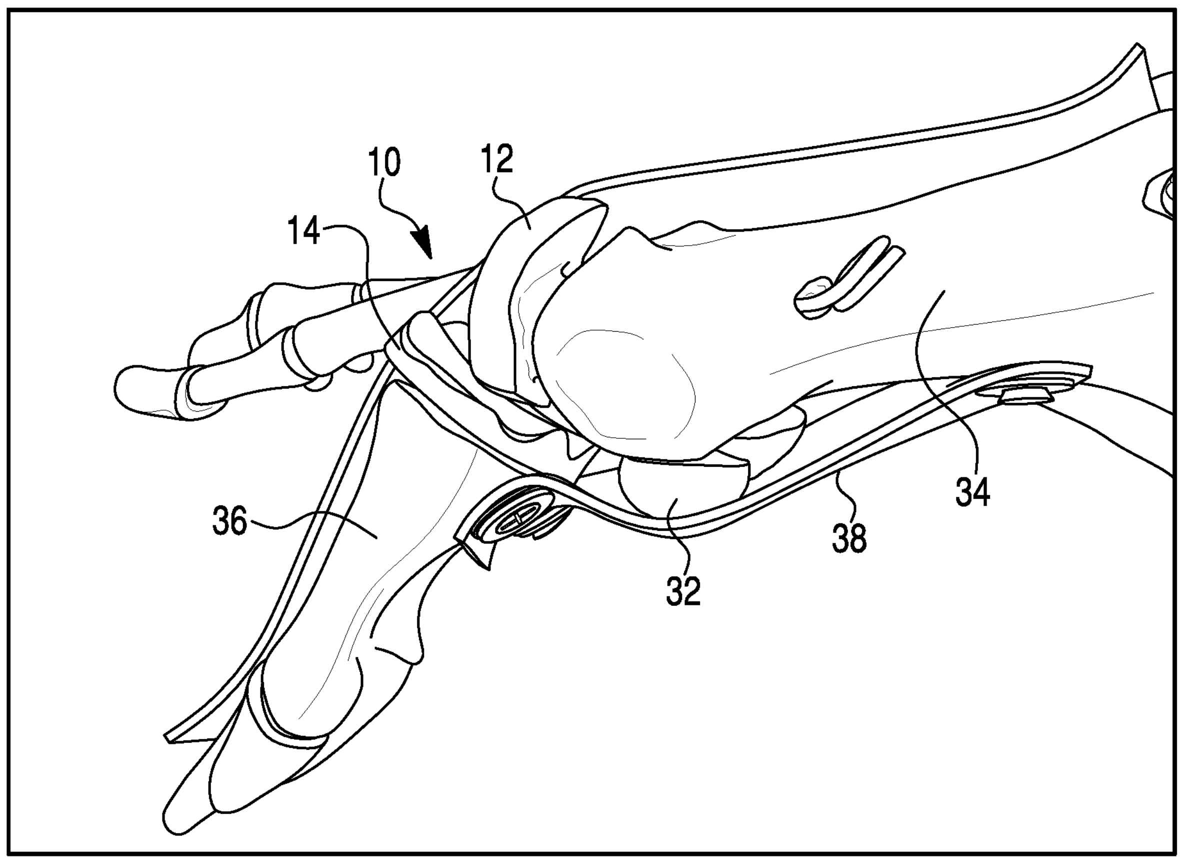
FIG. 5 depicts a side view of the first metatarsal and proximal phalange model with the exemplar joint implant of FIG. 1 placed at the first metatarsophalangeal joint, with the phalanges extended downward in the sagittal plane (plantar flexion)

As shown in FIG. 5, when the proximal phalange (36) rotates downward in a sagittal plane with respect to the metatarsal (34) (i.e., plantar flexion), phalangeal component (14) glides and pivots about the metatarsal component (12), while the sesamoid (32) moves in a proximal direction as the flexor hallucis brevis (38) retracts. FIG. 5 discloses how the joint implant (10) provides for a full or wide range of motion in the sagittal plane, allowing a patient to move the great toe in the sagittal plane.

However, joint implant (10) does not provide for full motion in a transverse plane, thereby keeping the proximal phalange (36) in-line with the metatarsal (34), in the same transverse plane. This has the effect of stabilizing a patient's great toe and preventing the great toe from deviating in a transverse direction towards the other toes. Impeding movement in the traverse plane may be desirable for correction of deformities of the great toe and/or for providing enhanced stability to the patient.

Figure 6:
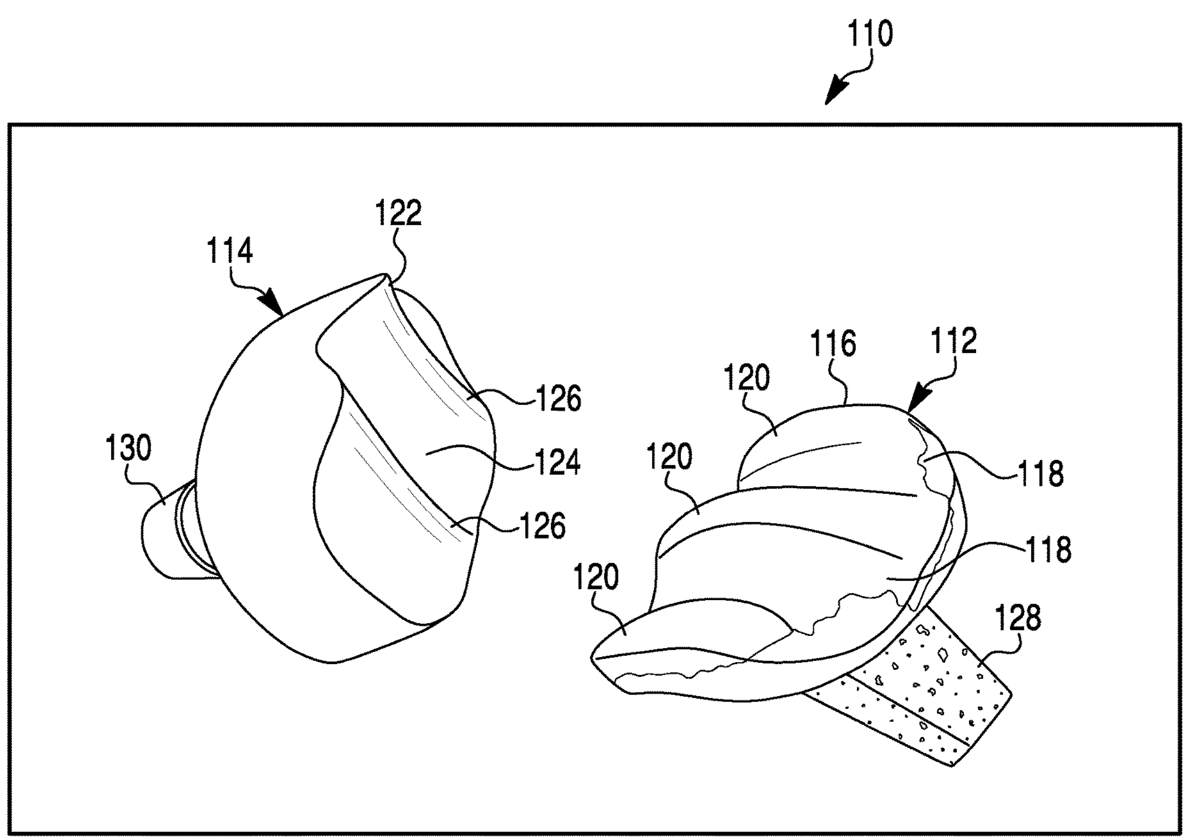
FIG. 6 depicts a second exemplar of an implant for the first metatarsophalangeal joint of the present invention.
Figure 7:
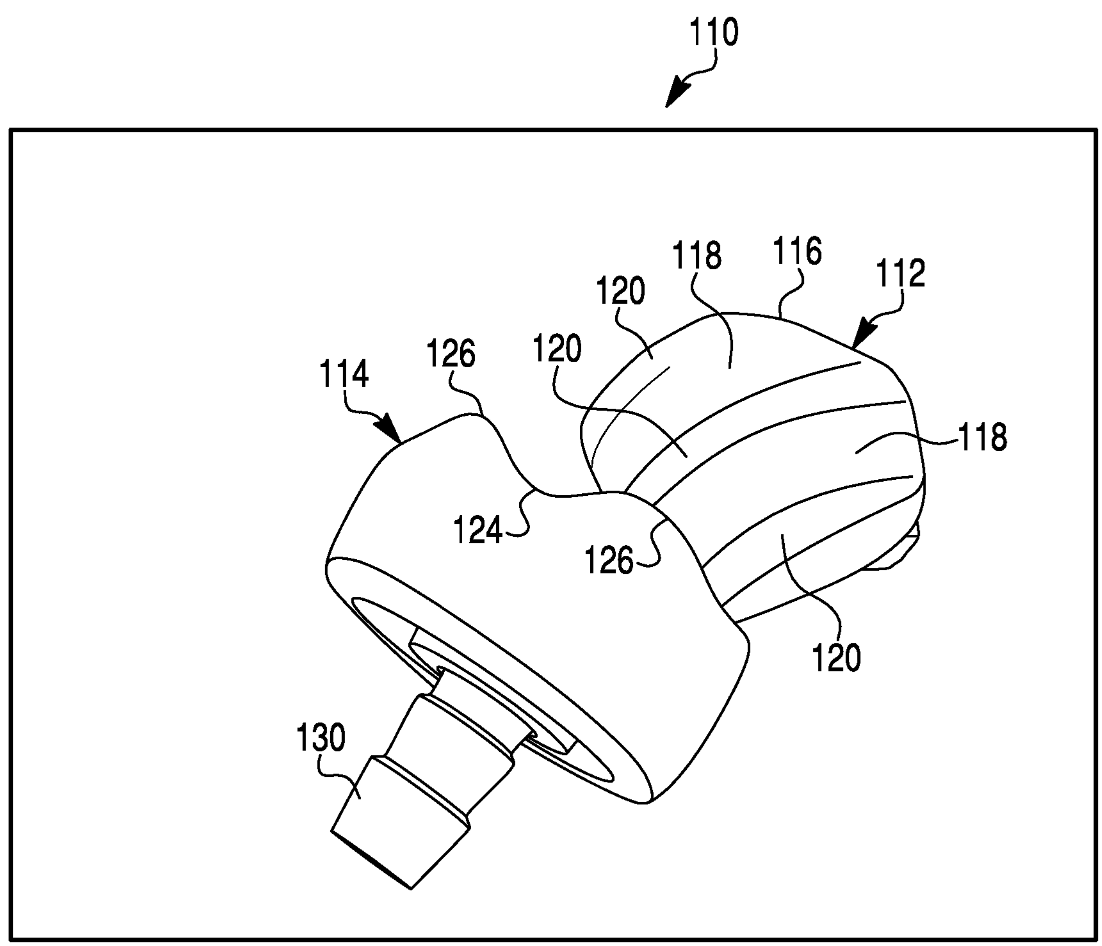
FIG. 7 depicts another view of the second exemplar joint implant of FIG. 6.

As shown in FIGS. 6 and 7, a second embodiment of an implant (110) for the first metatarsophalangeal joint is disclosed. The joint implant (110) comprises two components, a metatarsal component (112) and a phalangeal component (114). The metatarsal component (112) has an interfacing surface (116) that is ridged to include two valleys (118) and three ridges (120). The phalangeal component (114) has an interfacing surface (122) with a central valley (124) and two ridges (126). The metatarsal component (112) has a stem (128) for engaging with the metatarsal during placement, and the phalangeal component (114) has a threaded stem (130) for engaging with the proximal phalange during placement. The stem (128) of the metatarsal component (112) is compression fit into the metatarsal (34) during placement, but the stem (130) of the phalangeal component (114) is threaded to receive a screw 42, which passes through both the distal phalange (40) and proximal phalange (36). Threaded stem (130) is received by and secured within phalangeal component (114) by a ball socket, or similar, with permits threaded stem (130) to rotate slightly in all planes with respect to the phalangeal component (114). In one embodiment, threaded stem (130) rotates approximately five to seven degrees with respect to the phalangeal component (114) to allow for easier screw fixation.

The metatarsal component (112) of the modified joint implant (110) is similar to the metatarsal component (12) of joint implant (10). The phalangeal component (114) of the modified joint implant (110) differs from the phalangeal component (14) of joint implant (10) in that it has a greatly enhanced thickness, typically about 5 mm, and it is cannulated such that stem 130 is threaded to receive a bone screw 42.

During placement, the interfacing surface (116) of the metatarsal component (112) is received by the interfacing surface (122) of the phalangeal component (114) such that the central valley (124) of the phalangeal component (114) cradles the central ridge (120) of the metatarsal component (112), and the two ridges (126) of the phalangeal component (114) are cradled by the two valleys (118) of the metatarsal component (112). The engagement of the two interfacing surfaces (116, 122) allows for the phalangeal component (114) to rock up-and-down in a sagittal plane with respect to the metatarsal component (112), but impedes movement in a transverse plane because of the ridge-and-valley structure. As such, when the components (112, 114) are placed, the proximal phalange has a wide range of motion in the sagittal plane.

The components (112, 114) may be constructed of any appropriate biomaterial, including stainless steel, cobalt chromium alloy, chemically-pure titanium, titantium alloys, certain polymers, such as polyethylene (UHMW) and polymethylmethacrylate, silicone, certain ceramics, and carbon. In a preferred embodiment, the metatarsal component (112) is made of a cobalt chromium alloy, which is known to have excellent compressive strength, making it suitable for bearing surfaces such as interfacing surface (116), while the phalangeal component (114) is made of a UHMW material. Research tends to show that fabricating the components (112, 114) of different materials tends to enhance the longevity of the implant.

One of more of the stems (128, 130) of components (112, 114) may be powdered or coated with any appropriate material, including hydroxyapatite, porous titanium, calcium carbonate, and cobalt chromium. Applying such a coating to the stem is known to provide greater osteo-integration between the stem and the bone. One of more of the stems (128, 130) of components (112, 114) also may be serrated, to provide for stronger bone engagement and/or osteo-integration with the bone. The shape of the stems (128, 130) may be rounded, triangular, square, or any other shape as may be appropriate to engage with the bone.

The joint implant (110) depicted in FIGS. 6 and 7 is intended for use in a first metatarsophalangeal joint where the sesamoid bones (32) have fibrosed or fused to the metatarsal (34) and no longer glide about or move with respect to the metatarsal. Typically in this situation, the clinician will leave the sesamoids (32) undisturbed, but will remove the insertion of the flexor hallucis brevis (38) and the proximal end of the proximal phalange (36), where the flexor hallucis brevis attaches to the phalange. Because the proximal end of the proximal phalange (36) is removed, the enhanced thickness of phalangeal component (114) is necessary to build up the phalange such that the location of the first metatarsophalangeal joint and the length of the hallux are maintained.

Because the proximal end of the proximal phalange (36) is removed, one advantage of the phalangeal component (114) is that during placement, a clinician also may correct any deformation or deviation of the hallux as necessary to place the phalange and metatarsal (34) in line, including procedures such as an akin osteotomy of the proximal phalange (36) or fusion of the distal (40) and proximal phalanges (i.e., a hallux interphalangeal joint (IPJ) fusion). Because the joint implant (110) impedes transverse motion, aligning the proximal phalange and metatarsal has the effect of straightening the great toe.

Figure 8:
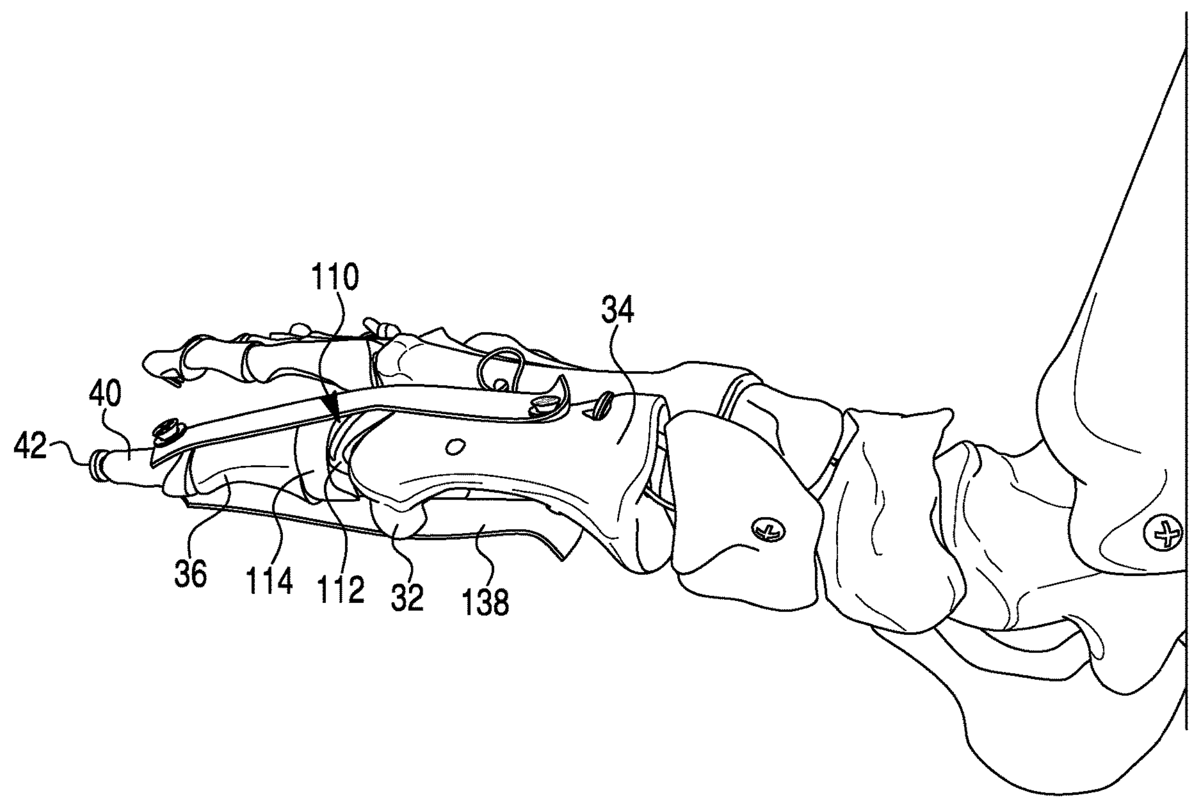
FIG. 8 depicts a side view of a model of the first metatarsal and proximal phalange with the exemplar joint implant of FIG. 6 placed at the first metatarsophalangeal joint of said model.
Figure 9:
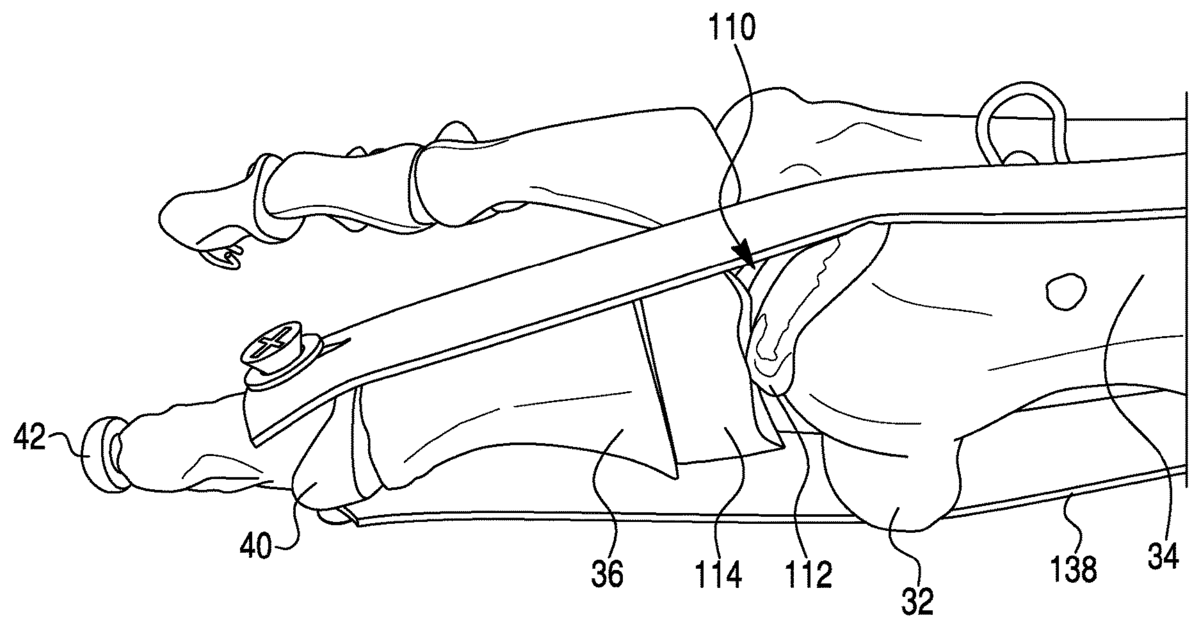
FIG. 9 depicts a closer side view of the second exemplar joint implant of FIG. 6 placed at the first metatarsophalangeal joint of the model.

As shown in FIGS. 8 and 9, after a clinician removes the flexor hallucis brevis (38) and the proximal end of the proximal phalange (36), the phalangeal component (114) is placed to abut the proximal phalange, with the threaded stem (130) being inserted into the phalange. A headed or headless screw (42) is passed through both the distal phalange (40) and the proximal phalange (36) and is received by the threaded stem (130) of the phalangeal component (114) of joint implant (110). The clinician can tighten the screw (42) as necessary to adequately secure the phalangeal component (114). Once the joint implant (110) is placed, the only tendon traveling underneath the phalanges (36, 40) and metatarsal (34) is the flexor hallucis longus (138), which spans under the metatarsal and attaches at the distal end of the distal phalange (40).

The headed or headless screw (42) may be constructed of any appropriate biomaterial, including stainless steel, cobalt chromium alloy, chemically-pure titanium, and titantium alloys. In a preferred embodiment, the screw is made of cobalt chromium alloy, or of the same material as the threaded stem (130) of phalangeal component (114). Those skilled in the art will appreciate that any appropriate size and type of screw may be used, which may vary among patients, but in a preferred embodiment, a cannulated 2.7 or 3.5 mm screw is used.

Figure 10:
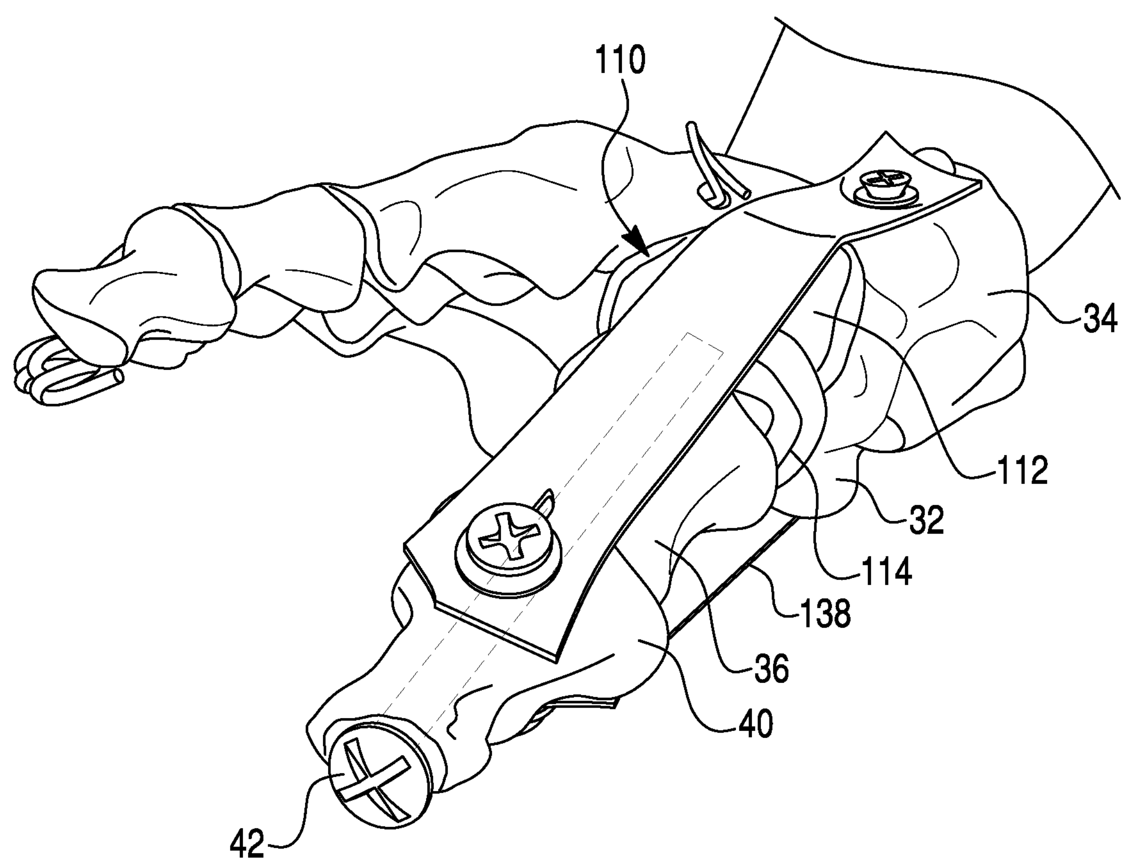
FIG. 10 depicts a model of the distal end of the distal phalange, with the head of the screw that secures the exemplar joint implant of FIG. 6, although those skilled in the art will appreciate that a headless screw may be used, in which case the screw is buried completely within the distal phalange.

During placement, and as best shown in FIG. 10, a clinician may use a standard surgical guide wire to determine the appropriate length of screw (42) to be used. Once the clinician removes the proximal end of the proximal phalange (36), the clinician may insert a guide wire through the proximal end of the distal phalange (40), and continue inserting the guide wire distally through the distal phalange and then back into the proximal phalange (36) and into the threaded stem (130) of the phalangeal component (114). By marking and measuring the length of inserted guide wire, a clinician may determine the appropriate size of screw (42) that will achieve adequate engagement with the stem (130) of the phalangeal component (114).

As shown in FIG. 10, the cannulated nature of the phalangeal component (114) provides another advantage in that the clinician also may correct certain deformities or deviation in the great toe by removing a wedge of bone and/or cartilage (Akin osteotomy) as necessary to align the phalanges, then tightening the screw to compress the distal phalange (40) against the proximal phalange (36). Additionally, because the threaded stem (130) rotates slightly (e.g., 5-7°) with respect to the phalangeal component (114), thereby making it easier to insert the guide wire and place the screw, a clinician may achieve significant compression between the distal (40) and proximal (36) phalanges and the implant.

As shown in FIGS. 11-14, a third embodiment of an implant (210) for the first metatarsophalangeal joint is disclosed. The joint implant (210) comprises two components, a metatarsal component (112) and a phalangeal component (214). The metatarsal component (112) in this embodiment is similar to that disclosed in the second embodiment above. The phalangeal component (214) has an interfacing surface (222) with a central valley (224) and two ridges (226). The phalangeal component (214) has a stem (230) for engaging with the proximal phalange (36) during placement. The stem (230) of the phalangeal component (214) is compression fit into the proximal phalange (36). A screw (242) passes through the center of the phalangeal component (214) and through the proximal phalange (36). The screw (242) is received by a threaded insert (244), which is placed within the distal phalange (40).

The screw (242) and threaded insert (244) may be constructed of any appropriate biomaterial, including stainless steel, cobalt chromium alloy, chemically-pure titanium, and titantium alloys. In a preferred embodiment, the screw (242) is made of cobalt chromium alloy, or of the same material as the threaded stem (244). Those skilled in the art will appreciate that any appropriate size and type of screw may be used, which may vary among patients, but in a preferred embodiment, a cannulated 2.7 or 3.5 mm screw is used.

One of more of the stems (128, 230) of components (112, 214) may be powdered or coated with any appropriate material, including hydroxyapatite, porous titanium, calcium carbonate, and cobalt chromium. Applying such a coating to the stem is known to provide greater osteo-integration between the stem and the bone. One of more of the stems (128, 230) of components (112, 214) also may be serrated, to provide for stronger bone engagement and/or osteo-integration with the bone. The shape of the stems (128, 230) may be rounded, triangular, square, or any other shape as may be appropriate to engage with the bone. In a preferred embodiment, the metatarsal component (112) is made of a cobalt chromium alloy, which is known to have excellent compressive strength, making it suitable for bearing surfaces such as interfacing surface (116), while the phalangeal component (214) is made of a UHMW material. Research tends to show that fabricating the components (112, 214) of different materials tends to enhance the longevity of the implant.

Figure 11:
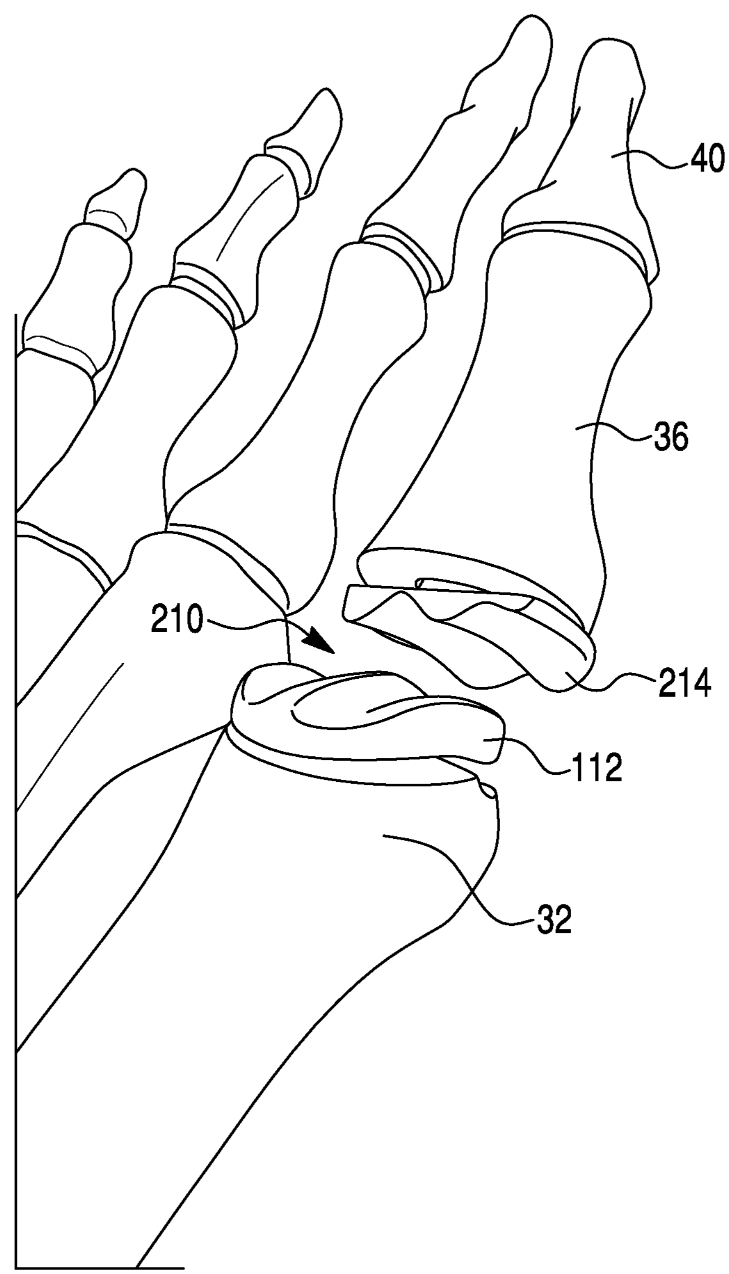
FIG. 11 depicts a third exemplar of an implant for the first metatarsophalangeal joint of the present invention.
Figure 12:
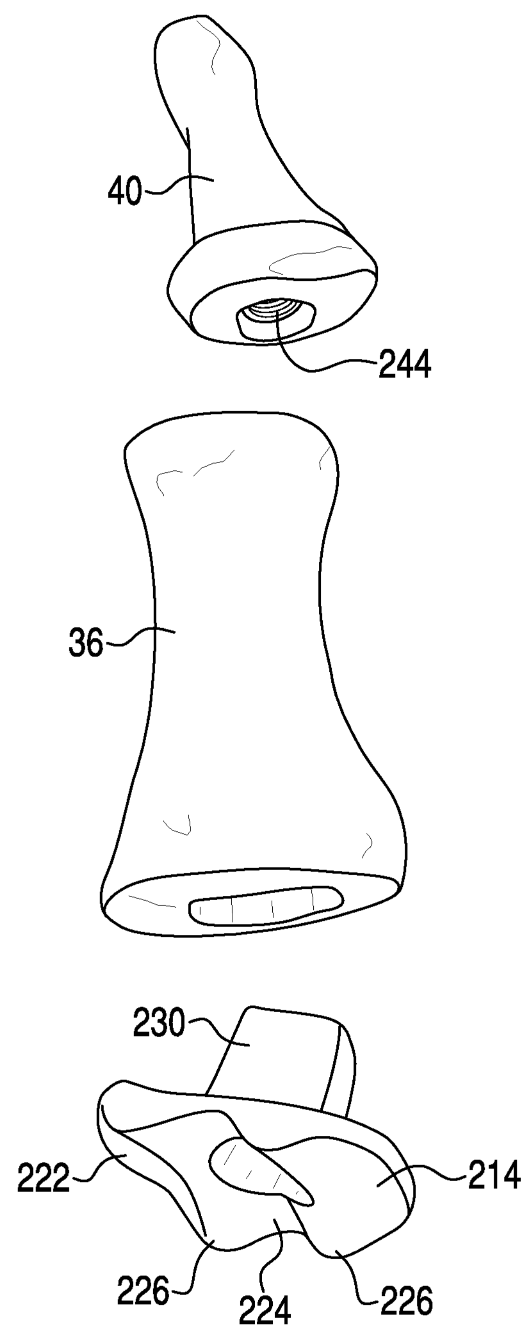
FIG. 12 depicts the components which may comprise the third exemplar joint implant of FIG. 11.
Figure 13:
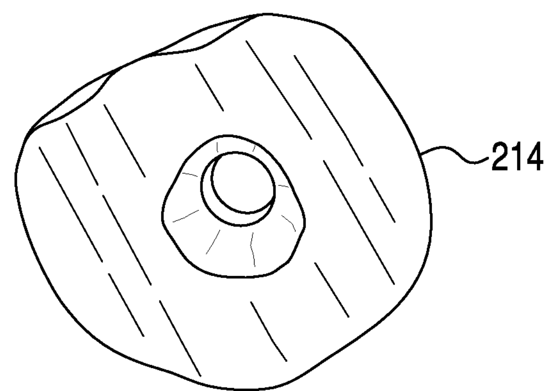
FIG. 13 depicts the distal phalange component of the exemplar joint implant of FIG. 11.
Figure 14:
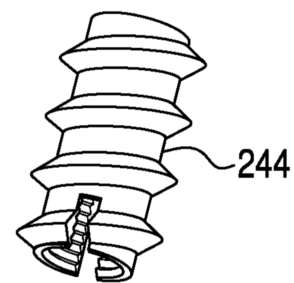
FIG. 14 depicts a threaded insert which may be used with the implant of FIG. 11 and may be inserted within the distal phalanx.
Figure 15:
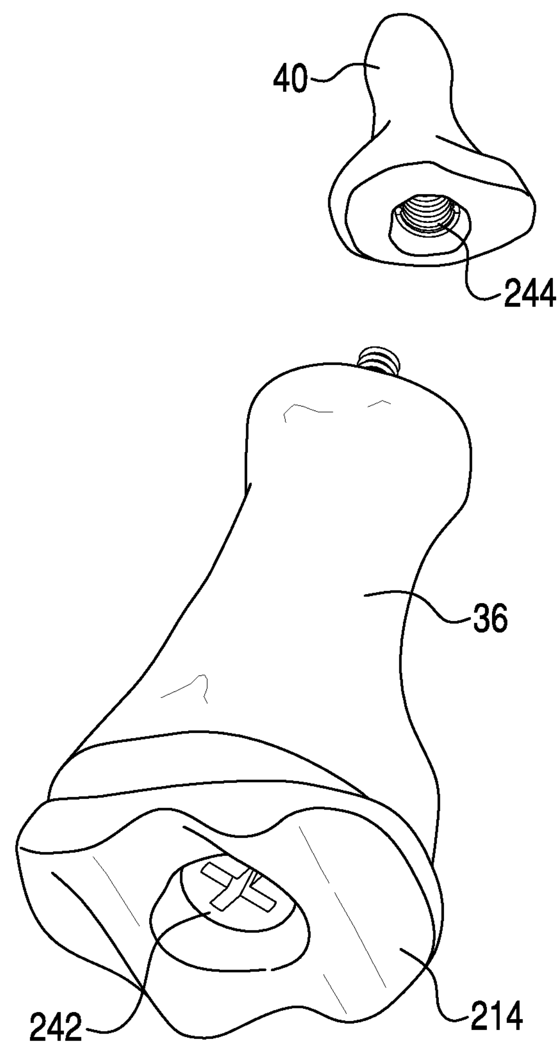
FIG. 15 depicts a perspective view of the exemplar joint implant of FIG. 11.

As shown in FIGS. 11 and 15, the head of the metatarsal (32) is skived at an angle, using a jig, to better mate with the metatarsal component (112) of the implant. The metatarsal dorsal curvature allows for an increase in "toe off" range of motion and prevents osteophyte growth. For example, as generally shown in FIGS. 11 and 15, the metatarsal head is skived at approximately 135 degrees. However, those skilled in the art will appreciate that the exact angle of skiving may vary among patients, depending on bone alignment and the clinician's determination of the patient's needs. The metatarsal component (112) is compression or press fit, as generally described in the second exemplar above. The phalangeal component (214) is cannulated and may be used with or without screw fixation.

The proximal phalange (36) is cut straight off the base by an appropriate amount, depending on how much decompression a clinician determines to be necessary or desirable. Typically, the proximal phalange is cut straight off the base by approximately 3-5 mm, though those skilled in the art will appreciate that the exact amount may vary among patients, depending on bone alignment and the clinician's determination of the patient's needs. The phalangeal component (214) is then fit onto the base of the proximal phalange (36) such that stem (130) is press or compression fit within the phalange.

If transverse plane motion needs to be corrected in the phalanx, then the interphalangeal joint ("IPJ") can be fused and a wedge of bone can be removed to align the hallux (thereby removing any deforming force), such that a bow strung extensor tendon will not exaggerate a transverse plane deformity.

A screw (242) is used to secure the phalangeal component (214) of the implant to the proximal and distal phalanges (36, 40). The screw (242) may be a bone screw that engages directly with the distal phalange (40). A guide wire is inserted into and through the distal phalange (40) and retrograded back into the proximal phalange (36) to measure for the appropriate length of screw (242) required to fuse the IPJ. Those skilled in the art will appreciate that any appropriate size and type of screw may be used, which may vary among patients, but in a preferred embodiment, a cannulated 2.7 or 3.5 mm screw is used.

Alternatively, a threaded insert (244) may be used to receive the screw (242) for securing the phalangeal component (214) of the implant. The threaded insert (244) is press or compression fit into the distal phalange (40) and is configured to receive and hold the screw (242). A guide wire is inserted into and through the distal phalange (40) and retrograded back into the proximal phalange (36) and into the threaded insert (244) to measure for the appropriate length of screw (242) required to fuse the IPJ.

Those skilled in the art will appreciate that the implant of the present invention also may be suitable or adapted for use with the first metacarpophalangeal joint, that is, with the thumb in a human hand. The first metacarpophalangeal joint has a bone structure similar to the first metatarsophalangeal joint, and many of the same deformities and deviations discussed herein with respect to the big toe also occur to the thumb. The implant of the present invention may be suitable or adapted for use within the first metacarpophalangeal joint of the thumb to correct deformities and/or deviations in the thumb. Those skilled in the art would appreciate that the sizing of the implant components and/or the types and sizes of screws used for fixation of the implant would vary among patients depending on bone structure and condition of the joint.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended representative claims.

What is claimed is:

1. An implant for the first metatarsophalangeal joint between the proximal phalange and the first metatarsal, the proximal phalange located proximally to the distal phalange and both phalanges moving in a sagittal plane perpendicular to a transverse plane, the implant comprising:

a metatarsal component for securing against the distal end of the first metatarsal, the metatarsal component having an interfacing surface with a plurality of ridges and valleys, the interfacing surface having at least two valleys;

a phalangeal component for abutting the proximal end of the proximal phalange, the phalangeal component having an interfacing surface with a plurality of ridges and valleys, the interfacing surface having at least two ridges, the phalangeal component further having a threaded stem;

a screw received by the threaded stem for securing the phalangeal component to the proximal and distal phalanges;

wherein the ridges of the interfacing surface of the metatarsal component are received by the valleys of the interfacing surface of the phalangeal component to provide for a full range of motion in the sagittal plane but impede motion in the transverse plane.

2. The implant of claim 1 wherein the metatarsal component has an interfacing surface having at least one valley for engaging with the phalangeal component, the valley running along a vertical axis from top to bottom of the interfacing surface of the metatarsal component.

3. The implant of claim 2 wherein the phalangeal component has an interfacing surface having two ridges for engaging with the metatarsal component.

4. The implant of claim 3 wherein the interfacing surface of the metatarsal component has two valleys for engaging with the two ridges of the phalangeal component.

5. The implant of claim 1 wherein the metatarsal component has a stem for insertion into the bone, the stem having a surface treated to promote osteo-integration with the bone.

6. The implant of claim 1 wherein the screw is a headless screw.

7. The implant of claim 1 wherein the screw may be tightened to compress a fusion of the distal phalange and the proximal phalange.

8. An implant for the first metatarsophalangeal joint between the proximal phalange and the first metatarsal, the proximal phalange located proximally to the distal phalange and both phalanges moving in a sagittal plane perpendicular to a transverse plane, the implant comprising:

a metatarsal component for securing against the distal end of the first metatarsal, the metatarsal component having an interfacing surface with a plurality of ridges and valleys, the interfacing surface having at least two valleys;

a phalangeal component for abutting the proximal end of the proximal phalange, the phalangeal component having an interfacing surface with a plurality of ridges and valleys, the interfacing surface having at least two ridges, the phalangeal component further having a stem for insertion into the proximal end of the proximal phalange;

a screw passing through the phalangeal component for securing the phalangeal component to the proximal and distal phalanges;

wherein the ridges of the interfacing surface of the metatarsal component are received by the valleys of the interfacing surface of the phalangeal component to provide for a full range of motion in the sagittal plane but impede motion in the transverse plane.

9. The implant of claim 8 wherein the metatarsal component has an interfacing surface having at least one valley for engaging with the phalangeal component, the valley running along a vertical axis from top to bottom of the interfacing surface of the metatarsal component.

10. The implant of claim 9 wherein the phalangeal component has an interfacing surface having two ridges for engaging with the metatarsal component.

11. The implant of claim 10 wherein the interfacing surface of the metatarsal component has two valleys for engaging with the two ridges of the phalangeal component.

12. The implant of claim 8 wherein the metatarsal component has a stem for insertion into the bone, the stem having a surface treated to promote osteo-integration with the bone.

13. The implant of claim 8 wherein the phalangeal component has a stem for insertion into the proximal phalange, the screw passing through a central portion of the stem.

14. The implant of claim 8 wherein the screw is received by a threaded insert to secure the phalangeal component of the implant to the proximal and distal phalanges.

15. The implant of claim 8 wherein the screw may be tightened to compress and fuse the distal phalange and the proximal phalange.

* * * * *